United States Patent
Ogura et al.

(10) Patent No.: US 12,144,619 B2
(45) Date of Patent: Nov. 19, 2024

(54) BLOOD MEASUREMENT DEVICE

(71) Applicants: LOOK TEC CO., LTD., Ota (JP); NATIONAL UNIVERSITY CORPORATION GUNMA UNIVERSITY, Maebashi (JP)

(72) Inventors: Hitoshi Ogura, Ota (JP); Koichi Takezawa, Ota (JP); Takayuki Asao, Maebashi (JP)

(73) Assignees: LOOK TEC CO., LTD, Ota (JP); NATIONAL UNIVERSITY CORPORATION GUNMA UNIVERSITY, Maebashi (JP)

( * ) Notice: Subject to any disclaimer, the term of this patent is extended or adjusted under 35 U.S.C. 154(b) by 164 days.

(21) Appl. No.: 17/928,605

(22) PCT Filed: Jun. 4, 2021

(86) PCT No.: PCT/JP2021/021421
§ 371 (c)(1),
(2) Date: Nov. 29, 2022

(87) PCT Pub. No.: WO2022/009577
PCT Pub. Date: Jan. 13, 2022

(65) Prior Publication Data
US 2023/0270359 A1    Aug. 31, 2023

(30) Foreign Application Priority Data

Jul. 6, 2020 (JP) .................................. 2020-116443
Jul. 6, 2020 (JP) .................................. 2020-116444

(51) Int. Cl.
*A61B 5/1455* (2006.01)
*A61B 5/145* (2006.01)

(52) U.S. Cl.
CPC ........ *A61B 5/1455* (2013.01); *A61B 5/14532* (2013.01)

(58) Field of Classification Search
CPC . A61B 5/0205; A61B 5/1455; A61B 5/14551; A61B 5/14552; A61B 5/14532;
(Continued)

(56) References Cited

U.S. PATENT DOCUMENTS 4,655,225 A  *  4/1987  Dahne .................. A61B 5/1455
                                                          600/316
4,883,953 A  *  11/1989  Koashi ............... A61B 5/14532
                                                          250/341.8
(Continued)

FOREIGN PATENT DOCUMENTS

CN    101454654 A    6/2009
CN    111373267 A    7/2020
(Continued)

OTHER PUBLICATIONS

International Search Report dated Jul. 6, 2020, issued in counterpart application No. PCT/JP2021/021421. (14 pages).
(Continued)

*Primary Examiner* — Chu Chuan Liu
(74) *Attorney, Agent, or Firm* — WHDA, LLP

(57) ABSTRACT

A blood measurement device (10) includes a light emitting part (11) that emits a light beam that is to transmit through a measurement site (18), a light receiving part (19) that receives the light beam that has transmitted through the measurement site (18), an integrating sphere part (14) interposed in an optical path along which the light beam emitted from the light emitting part (11) reaches the light receiving part (19), the integrating sphere part (14) having formed inside a reflection surface (26) that reflects the light beam, a light entry part (23) which is an opening provided at the
(Continued)

integrating sphere part (14) and through which the light beam applied from the light emitting part (11) enters an inside of the integrating sphere part (14), and a light exit part (16) which is an opening provided at the integrating sphere part (14) and through which the light beam reflected by the reflection surface (26) of the integrating sphere part (14) is emitted from the integrating sphere part (14) toward the measurement site (18).

5 Claims, 8 Drawing Sheets

(58) Field of Classification Search
CPC ............ A61B 5/14535; A61B 5/14542; A61B 5/14546; A61B 5/1495
See application file for complete search history.

(56) References Cited

U.S. PATENT DOCUMENTS

| | | | | |
|---|---|---|---|---|
| 5,178,142 | A * | 1/1993 | Harjunmaa | A61B 5/1455 600/316 |
| 5,879,294 | A * | 3/1999 | Anderson | A61B 5/14551 600/323 |
| 2009/0209836 | A1 | 8/2009 | Niwayama | |
| 2014/0030737 | A1 | 1/2014 | Holmes et al. | |
| 2016/0367173 | A1 * | 12/2016 | Dalvi | A61B 5/1455 |
| 2020/0319218 | A1 | 10/2020 | Nobuki et al. | |

FOREIGN PATENT DOCUMENTS

| | | | |
|---|---|---|---|
| JP | 1-131436 | A | 5/1989 |
| JP | 9-049794 | A | 2/1997 |
| JP | 3093871 | B2 | 10/2000 |
| JP | 3692751 | B2 | 9/2005 |
| JP | 2009-233285 | A | 10/2009 |
| JP | 2012-105809 | A | 6/2012 |
| JP | 2018-139952 | A | 9/2018 |
| JP | 2021-7486 | A | 1/2021 |
| TW | 201831881 | A | 9/2018 |

OTHER PUBLICATIONS

Office Action dated Mar. 4, 2024, issued in counterpart JP application No. 2020-116444, with English translation. (6 pages).

Office Action dated Mar. 4, 2024, issued in counterpart TW application No. 110122940. (4 pages).

* cited by examiner (A)

(B)

(A)

(B)

(A)

(B)

(A)

(B)

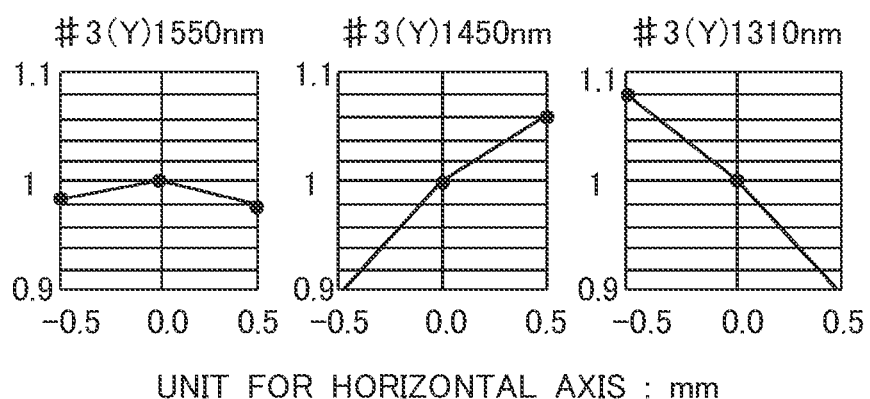
FIG.8 (A) (B) (C)
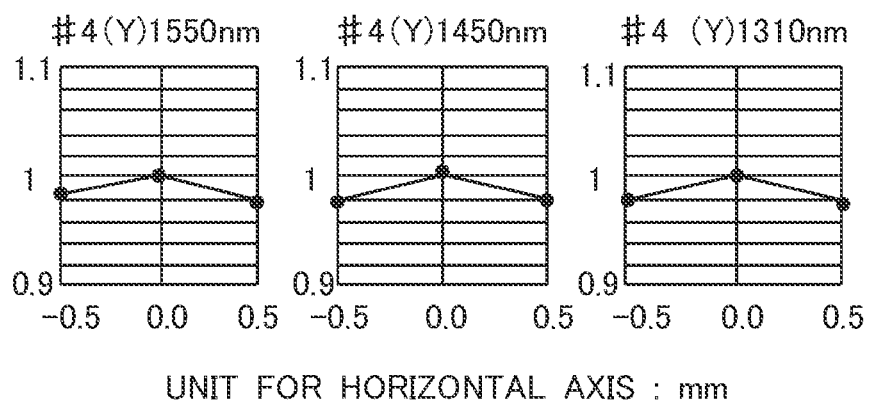

BLOOD MEASUREMENT DEVICE

TECHNICAL FIELD

The present invention relates to a blood measurement device that optically measures the amount of a component contained in blood inside a measurement site of the human body or the like.

BACKGROUND ART

There are an invasive approach and a non-invasive approach as methods for detecting sugar inside a measured site. In a method using an invasive approach, blood is drawn from, e.g., a fingertip of the human body, and the blood is used to measure a glucose level. In a method using a non-invasive approach, no blood is drawn from the human body, and a glucose level is measured with a sensor placed outside of the human body. While an invasive approach is common in order to calculate an accurate glucose level, a calculation device using a non-invasive approach is desired so as to mitigate pain and improve convenience for a user.

A known example of a device for measuring a glucose level using a non-invasive approach is one that performs optical measurement by applying near-infrared light or the like to the human body.

Also, as a device that optically measures a glucose level, there is one that detects a difference in an amount of near-infrared light absorbed by glucose. Specifically, this device causes near-infrared light to transmit through a given site and measures a glucose level from the amount of light transmitted (for example, Patent Literatures 1 and 2).

However, the non-invasive glucose-level measurement device described in each of the above patent literatures has a problem of not necessarily being able to measure an accurate glucose level.

Specifically, the measurement technique described in Patent Literature 1 calculates a glucose level using a glucose oxidase method and thus has a problem of a glucose level calculation being complicated. Meanwhile, the measurement technique described in Patent Literature 2 measures a glucose level using an optical approach, but only to a level of being able to determine a possibility of diabetes, not to a level of being able to measure a glucose level quantitatively.

In view of the above, the applicant of the present application invented the device described in Patent Literature 3. The device has a light receiving part having a plurality of light emitting portions of different wavelengths, an actuator, and a computation and control part that estimates a glucose level and controls operation of the actuator. The computation and control part causes the actuator to move, onto an optical axis, the light emitting portions that emit light beams to a measurement site, the optical axis being defined to penetrate through the measurement site. In this device, an optical path along which the light beams of different wavelengths travel and the length of the optical path can be uniformized. Owing to the optical conditions thus being uniformed between the light beams, the amount of a component contained in blood can be measured accurately based on the light reception intensities of the light beams that have transmitted through the measurement site.

CITATION LIST

Patent Literature

Patent Literature 1: Japanese Patent No. 3093871
Patent Literature 2: Japanese Patent No. 3692751
Patent Literature 3: Japanese Patent Application 2019-121746

SUMMARY OF THE INVENTION

Problem to be Solved by the Invention

However, the invention described in Patent Literature 3 requires an actuator for moving the light emitting part on the optical axis and hence may lead to problems such as higher costs, complication, and a higher failure rate of the device as a whole. Further, the invention described in Patent Literature 3 has a motor as the actuator and for this reason has a problem of the motor consuming a large amount of power during operation. This problem is also expected in a case of measuring a physical quantity other than a glucose level.

The present invention has been made in view of such problems and has an object to provide a blood measurement device that can be without an actuator for moving a light emitting part.

Means for Solving the Problem

A blood measurement device according to the present invention is a blood measurement device that measures a component contained in blood based on a light beam that has transmitted through or been reflected by a measurement site, the blood measurement device including: a light emitting part that emits the light beam that is to transmit through or be reflected by the measurement site; a light receiving part that receives the light beam that has transmitted through or been reflected by the measurement site; an integrating sphere part interposed in an optical path along which the light beam emitted from the light emitting part reaches the light receiving part, the integrating sphere part having formed inside a reflection surface that reflects the light beam; a light entry part which is an opening provided at the integrating sphere part and through which the light beam applied from the light emitting part enters an inside of the integrating sphere part; and a light exit part which is an opening provided at the integrating sphere part and through which the light beam reflected by the reflection surface of the integrating sphere part is emitted from the integrating sphere part toward the measurement site.

In the blood measurement device according to the present invention, the light emitting part applies a first light beam and a second light beam from a first light emitting part and a second light emitting part, respectively, the second light beam having a wavelength different from that of the first light beam, the reflection surface of the integrating sphere part reflects the first light beam and the second light beam, through the light exit part of the integrating sphere part, the first light beam and the second light beam are applied toward the measurement site and the light receiving part, and the light receiving part receives the first light beam and the second light beam.

In the blood measurement device according to the present invention, the reflection surface of the integrating sphere part has a spherical surface shape.

In the blood measurement device according to the present invention, the blood measurement device further includes: a light monitor opening part which is an opening provided at the integrating sphere part and through which part of the light beam entering the integrating sphere part through the light entry part and getting reflected by the reflection surface is emitted to an outside; a monitor light receiving part that receives the light beam emitted through the light monitor opening part; and a computation and control part that controls intensity of the light beam emitted from the light emitting part based on an output from the monitor light receiving part.

In the blood measurement device according to the present invention, the reflection surface is a coarse surface.

In the blood measurement device according to the present invention, the light emitting part applies a first light beam, a second light beam, and a third light beam from a first light emitting part, a second light emitting part, and a third light emitting part, respectively, the second light beam having a wavelength different from that of the first light beam, the third light beam having a wavelength different from those of the first and second light beams, the reflection surface of the integrating sphere part reflects the first light beam, the second light beam, and the third light beam, through the light exit part of the integrating sphere part, the first light beam, the second light beam, and the third light beam are applied toward the measurement site and the light receiving part, and the light receiving part receives the first light beam, the second light beam, and the third light beam.

A blood measurement device according to the present invention is a blood measurement device that measures a component contained in blood based on a light beam that has transmitted through or been reflected by a measurement site, the blood measurement device including: a light emitting part that emits the light beam that is to transmit through or be reflected by the measurement site; a light receiving part that receives the light beam that has transmitted through or been reflected by the measurement site; a light emission support part that supports the light emitting part; a light reception support part that supports the light receiving part; and a movement press part situated movably between the light emission support part and the light reception support part, in which the movement press part brings the blood measurement device into an insertion mode by being moved closer to the light emission support part, the insertion mode being a mode where the measurement site is insertable onto an optical path of the light beam, and the movement press part brings the blood measurement device into a measurement mode by being moved closer to the light reception support part and pressed against the measurement site, the measurement mode being a mode where the light beam is applied to the measurement site to perform measurement.

In the blood measurement device according to the present invention, a moving mechanism for moving the movement press part has a cam shaft, a cam that is attached to the cam shaft in such a manner as not to be relatively rotatable and that moves the movement press part, and a lever attached to the cam shaft in such a manner as not to be relatively rotatable.

In the blood measurement device according to the present invention, a spring is placed to exert biasing force to the movement press part.

In the blood measurement device according to the present invention, the movement press part has an insertion hole, the light emission support part has a tubular part through which the light beam passes, and in the insertion mode and the measurement mode, the tubular part is inserted in the insertion hole.

In the blood measurement device according to the present invention, the movement press part has a movement abutment part, the light reception support part has a light-reception-side abutment part, in the insertion mode, the movement abutment part and the light-reception-side abutment part are away from each other by a distance equal to or more than a thickness of the measurement site, and in the measurement mode, the movement abutment part and the light-reception-side abutment part are close to each other by a distance equal to or less than the thickness of the measurement site.

Effect of the Invention

A blood measurement device according to the present invention is a blood measurement device that measures a component contained in blood based on a light beam that has transmitted through or been reflected by a measurement site, the blood measurement device including: a light emitting part that emits the light beam that is to transmit through or be reflected by the measurement site; a light receiving part that receives the light beam that has transmitted through or been reflected by the measurement site; an integrating sphere part interposed in an optical path along which the light beam emitted from the light emitting part reaches the light receiving part, the integrating sphere part having formed inside a reflection surface that reflects the light beam; a light entry part which is an opening provided at the integrating sphere part and through which the light beam applied from the light emitting part enters an inside of the integrating sphere part; and a light exit part which is an opening provided at the integrating sphere part and through which the light beam reflected by the reflection surface of the integrating sphere part is emitted from the integrating sphere part toward the measurement site. Thus, according to the present invention in which the integrating sphere part is interposed in the optical path, the light beams uniformed by being reflected by the reflection surface of the integrating sphere part can be uniformly applied to the measurement site in a columnar region. This helps prevent light beams applied to the light receiving element from being drastically decreased in intensity even if the position of the light emitting element that applies the light beams is somewhat displaced from its designed location.

In the blood measurement device according to the present invention, the light emitting part applies a first light beam and a second light beam from a first light emitting part and a second light emitting part, respectively, the second light beam having a wavelength different from that of the first light beam, the reflection surface of the integrating sphere part reflects the first light beam and the second light beam, through the light exit part of the integrating sphere part, the first light beam and the second light beam are applied toward the measurement site and the light receiving part, and the light receiving part receives the first light beam and the second light beam. Thus, according to the present invention, if a first light beam and a second light beam having different wavelengths are applied from the first light emitting part and the second light emitting part, an actuator is usually needed to move the first light emitting part and the second light emitting part onto the optical axis. However, in the present invention, as described above, a light beam uniformed by being reflected by the reflection surface of the integrating sphere part is uniformly applied to the measurement site in a columnar region, and thus, a plurality of light beams of different wavelengths can be applied toward the measurement site and the light receiving part along the optical path without needing an actuator.

In the blood measurement device according to the present invention, the reflection surface of the integrating sphere part has a spherical surface shape. Thus, according to the present invention in which the reflection surface of the integrating sphere part has a spherical surface shape, a light beam reflected by the reflection surface a plurality of times can be uniformly applied toward the measurement site and the light receiving part through the light exit part.

In the blood measurement device according to the present invention, the blood measurement device further includes: a light monitor opening part which is an opening provided at the integrating sphere part and through which part of the light beam entering the integrating sphere part through the light entry part and getting reflected by the reflection surface is emitted to an outside; a monitor light receiving part that receives the light beam emitted through the light monitor opening part; and a computation and control part that controls intensity of the light beam emitted from the light emitting part based on an output from the monitor light receiving part. Thus, according to the present invention, the intensity of a light beam reflected by the reflection surface is measured with the monitor light receiving part, and based on the result, the computation and control part adjusts the intensity of light applied from the light emitting part, thereby allowing light applied to the measurement site and the light receiving part to have a predetermined intensity.

In the blood measurement device according to the present invention, the reflection surface is a coarse surface. Thus, according to the present invention in which the reflection surface of the integrating sphere part is a coarse surface, a light beam is diffusely reflected by the reflection surface effectively, and a columnar light beam can be applied toward the measurement site and the light receiving part through the light exit part.

In the blood measurement device according to the present invention, the light emitting part applies a first light beam, a second light beam, and a third light beam from a first light emitting part, a second light emitting part, and a third light emitting part, respectively, the second light beam having a wavelength different from that of the first light beam, the third light beam having a wavelength different from those of the first and second light beams, the reflection surface of the integrating sphere part reflects the first light beam, the second light beam, and the third light beam, through the light exit part of the integrating sphere part, the first light beam, the second light beam, and the third light beam are applied toward the measurement site and the light receiving part, and the light receiving part receives the first light beam, the second light beam, and the third light beam. Thus, according to the present invention which uses the first light beam, the second light beam, and the third light beam, a glucose level can be measured with higher precision.

A blood measurement device according to the present invention is a blood measurement device that measures a component contained in blood based on a light beam that has transmitted through or been reflected by a measurement site, the blood measurement device including: a light emitting part that emits the light beam that is to transmit through or be reflected by the measurement site; a light receiving part that receives the light beam that has transmitted through or been reflected by the measurement site; a light emission support part that supports the light emitting part; a light reception support part that supports the light receiving part; and a movement press part situated movably between the light emission support part and the light reception support part, in which the movement press part brings the blood measurement device into an insertion mode by being moved closer to the light emission support part, the insertion mode being a mode where the measurement site is insertable onto an optical path of the light beam, and the movement press part brings the blood measurement device into a measurement mode by being moved closer to the light reception support part and pressed against the measurement site, the measurement mode being a mode where the light beam is applied to the measurement site to perform measurement. Thus, according to the present invention which has the movement press part that moves between the insertion mode and the measurement mode, the movement press part can make the measurement site have a predetermined thickness by pressing the measurement site in the measurement mode, which allows blood-related parameters such as a blood sugar level to be accurately measured.

In the blood measurement device according to the present invention, a moving mechanism for moving the movement press part has a cam shaft, a cam that is attached to the cam shaft in such a manner as not to be relatively rotatable and that moves the movement press part, and a lever attached to the cam shaft in such a manner as not to be relatively rotatable. Thus, according to the present invention, a user can freely change the relative distance between the light emission support part and the light reception support part by rotating the lever and thereby rotating the cam.

In the blood measurement device according to the present invention, a spring is placed to exert biasing force to the movement press part. Thus, according to the present invention, the position of the movement press part can be controlled precisely using the pressing force of the cam and the biasing force of the spring.

In the blood measurement device according to the present invention, the movement press part has an insertion hole, the light emission support part has a tubular part through which the light beam passes, and in the insertion mode and the measurement mode, the tubular part is inserted in the insertion hole. Thus, according to the present invention in which the tubular part is inserted in the insertion hole in the insertion mode and the measurement mode, the optical path can be covered by the tubular part at all times.

In the blood measurement device according to the present invention, the movement press part has a movement abutment part, the light reception support part has a light-reception-side abutment part, in the insertion mode, the movement abutment part and the light-reception-side abutment part are away from each other by a distance equal to or more than a thickness of the measurement site, and in the measurement mode, the movement abutment part and the light-reception-side abutment part are close to each other by a distance equal to or less than the thickness of the measurement site. Thus, according to the present invention, a measurement site can be easily inserted to between the movement abutment part and the light-reception-side abutment part in the insertion mode, and the measurement site is sandwiched between the movement abutment part and the light-reception-side abutment part to have a certain thickness of the measurement site in the measurement mode, which enables alignment of the optical conditions and thus makes it possible to measure a glucose level accurately.

BRIEF DESCRIPTION OF THE DRAWINGS

FIG. 8 is graphs showing effects related to the longitudinal direction by the blood measurement device according to the embodiment of the present invention, FIGS. 8(A), 8(B), and 8(C) showing results for the blood measurement device of the comparative example having no integrating sphere part and FIGS. 8(D), 8(E), and 8(F) showing results for the present embodiment having the integrating sphere part.

MODES FOR CARRYING OUT THE INVENTION

A blood measurement device 10 according to an embodiment of the present invention is described in detail below based on the drawings. In the following description, the same reference number is basically used for the same members to omit repetitive descriptions. In the present embodiment, a glucose level is employed as an example of the amount of a component contained in blood measured by the blood measurement device 10.

Figure 1:
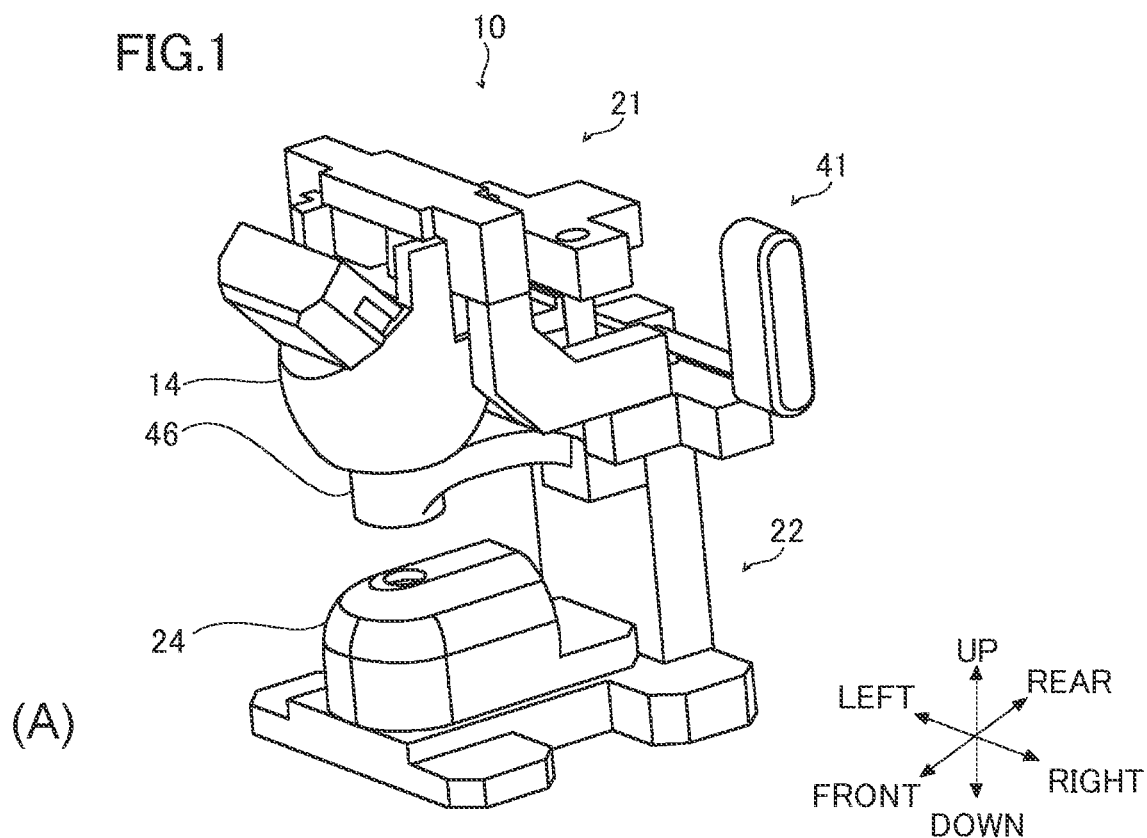
FIG. 1 is a diagram showing a blood measurement device according to an embodiment of the present invention, FIG. 1(A) being a perspective view showing the blood measurement device and FIG. 1(B) being a diagram showing an example of a measurement site.
Figure 1:
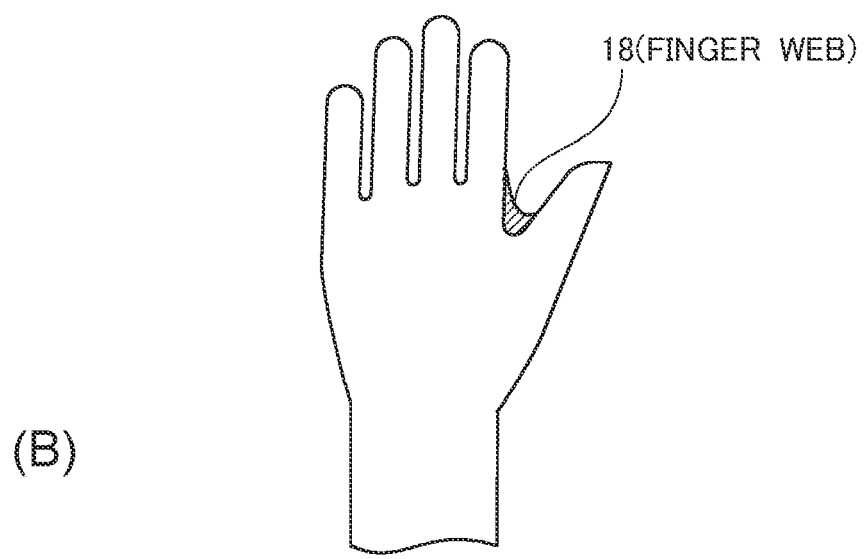

FIG. 1 is a diagram showing a schematic configuration of a blood measurement device 10. FIG. 1(A) is a perspective view of the blood measurement device 10, and FIG. 1(B) is a diagram showing an example of a measurement site 18.

With reference to FIG. 1(A), the blood measurement device 10 mainly has a light emitting part 11, a light receiving part 19, and an integrating sphere part 14. The light emitting part 11 is placed inside the integrating sphere part 14 and is thus not shown in FIG. 1(A). Similarly, the light receiving part 19 is placed inside a light reception cover part 24 and is thus not shown.

The function of the blood measurement device 10 is to apply light beams to the human body, which is the measurement site 18, and measure a glucose level in the human body using a non-invasive approach from the intensities of the light beams that have transmitted through or been reflected by the human body. Here, a glucose level is a blood or interstitial glucose level. Also, a glucose level is sometimes referred to as a blood sugar level or the like.

A schematic configuration of the blood measurement device 10 has a light emission support part 21 that supports the light emitting part 11, a light reception support part 22 that supports the light receiving part 19, a movement press part 46, and a moving mechanism 41 that moves the movement press part 46 in the up-down directions. A specific configuration of the blood measurement device 10 will be described later with reference to FIG. 2 and the like.

Referring to FIG. 1(B), a fingertip, an earlobe, a finger web, or the like can be used as the measurement site 18 for measuring a glucose level. Among these, a finger web is preferable as the measurement site 18 because a finger web contains only a small amount of fat, does not vary in its thickness much between individuals, and has no thick vein formed therein.

As will be described later, to measure a glucose level using the blood measurement device 10, a user places their finger web as the measurement site 18 between the light reception cover part 24 and the movement press part 46, light beams are caused to transmit through the finger web, and a glucose level is calculated from the intensities of the light beams that have transmitted through the finger web. A method for measuring a glucose level will be described in detail later.

Figure 2:
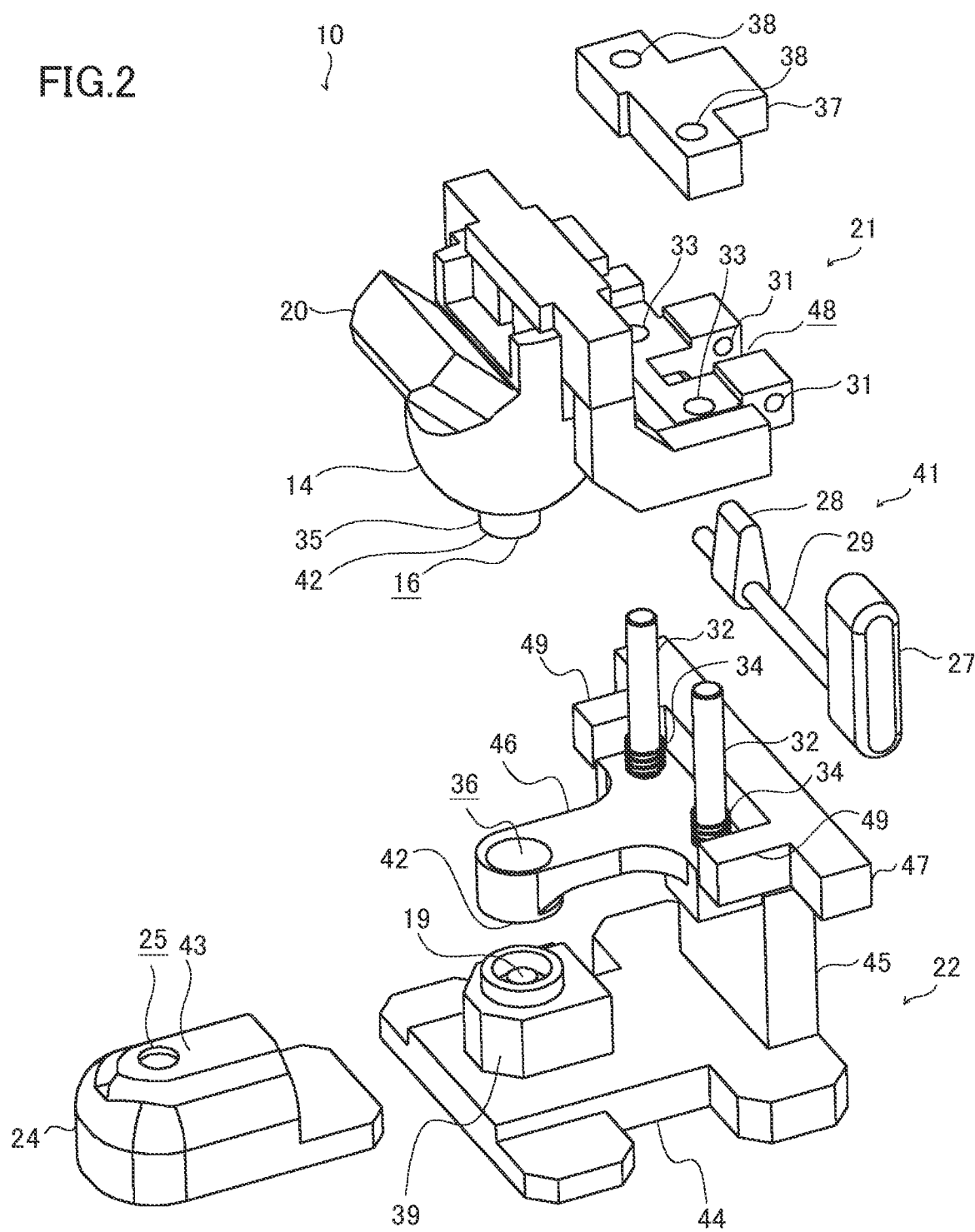
FIG. 2 is an exploded perspective view showing the blood measurement device according to the embodiment of the present invention.
Figure 2:
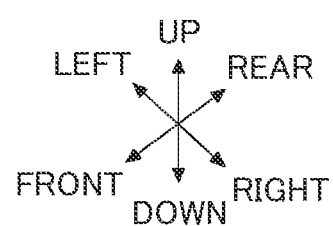

FIG. 2 is an exploded perspective view showing the blood measurement device 10. As described earlier, the blood measurement device 10 mainly has the light emission support part 21, the light reception support part 22, the movement press part 46, and the moving mechanism 41.

The light emission support part 21 is a part that supports, e.g., the integrating sphere part 14 and the light emitting part 11. The integrating sphere part 14 and a monitor light receiving part 20 are fixed to a front portion of the light emission support part 21. Also, support shaft insertion holes 33 are formed, penetrating a rear side of the light emission support part 21 in the up-down direction. Two support shaft insertion holes 33 are formed here. A support shaft 32 to be described later is inserted through each support shaft insertion hole 33. Also, cam shaft insertion holes 31 are formed, penetrating through a rear end portion of the light emission support part 21 in the left-right direction. A cam shaft 29 to be described later is inserted through the cam shaft insertion holes 31. Further, a center portion, in the left-right direction, of the rear end portion of the light emission support part 21 is notched to form a notch part 48. A cam 28 to be described later is housed in the notch part 48. The lower surface of the light emission support part 21 is fixed to the upper surface of the light reception support part 22.

The integrating sphere part 14 is fixed to a front portion of the light emission support part 21. The integrating sphere part 14 has a function to diffusely reflect light applied from the light emitting part 11, which is not shown in FIG. 2, and thereby uniform the light. The monitor light receiving part 20 is attached to a front upper portion of the integrating sphere part 14. The monitor light receiving part 20 is an element that receives a light beam from the inside of the integrating sphere part 14 and monitors the intensity of the light beam.

The light reception support part 22 has, from below, a seat part 44, a pillar part 45, and a light reception support upper part 47.

The seat part 44 is a seat that supports the entire blood measurement device 10, and has a light reception placement part 39 attached to its upper surface. The light receiving part 19 is placed on the upper surface of the light reception placement part 39.

The light reception cover part 24 is a hollow member on the upper surface of the seat part 44, covering the light reception placement part 39 and the light receiving part 19. A substantially circular opening is formed in the upper surface of the light reception cover part 24 to form a light reception entry part 25. When seen from above, the light receiving part 19 is housed within the range of the light reception entry part 25. Such a configuration allows a light beam applied from the light emitting part 11, which is not shown in FIG. 2, to be applied to the light receiving part 19 through the light reception entry part 25. Also, a substantially planar light-reception-side abutment part 43 is formed on the upper surface of the light reception cover part 24, surrounding the light reception entry part 25. The light-reception-side abutment part 43 is a part where the lower surface of a user's finger web touches during the glucose level measurement.

The pillar part 45 is a member extending upward from a rear end of the seat part 44, substantially in the shape of a wall.

The light reception support upper part 47 is a part formed on the upper portion of the pillar part 45 and is a part to which the light emission support part 21 is fixed. Also, areas near the respective end portions of the light reception cover part 24 in the left-right direction are protruded frontward to form guide parts 49.

The movement press part 46 is situated frontward of the light reception support upper part 47 in such a manner as to be movable in the up-down direction. The rear side surface of the movement press part 46 abuts against the front surface of the light reception support upper part 47. Also, the left side surface and the right side surface of a rear end portion of the movement press part 46 abut against the guide parts 49. This configuration allows favorable guidance of the movement of the movement press part 46 in the up-down direction during use.

An insertion hole 36 is formed, circularly penetrating through the front end of the movement press part 46. A tubular part 35 of the integrating sphere part 14 is movably inserted into the insertion hole 36. A movement abutment part 42 is formed on the lower surface of an area near the front end of the movement press part 46. During use, the movement abutment part 42 is pressed against the upper surface of a finger web, which is the measurement site 18, from above.

The columnar support shafts 32 are fixed to the upper surface of a rear end portion of the movement press part 46. Here, two support shafts 32 are provided upright. The support shafts 32 are inserted through springs 34. The springs 34 are biasing means that bias the movement press part 46 downward, with their lower ends being in abutment with the upper surface of the movement press part 46 and their upper ends being in abutment with the upper surface of the light emission support part 21. Also, middle portions of the support shafts 32 are slidably inserted through the support shaft insertion holes 33 of the light emission support part 21. Further, the upper ends of the support shafts 32 are fixed to abutment insertion holes 38 of an abutment part 37. This configuration allows the movement press part 46, the support shafts 32, and the abutment part 37 to move in the up-down direction while being biased by the support shafts 32 according to the operation of a lever 27.

The abutment part 37 is a member situated above the light emission support part 21, and as described above, has the abutment insertion holes 38 formed therein to fix the upper ends of the support shafts 32. Also, the cam 28 to be described below abuts against the lower surface of a rear portion of the abutment part 37.

The moving mechanism 41 has the cam shaft 29, the cam 28, and the lever 27. The moving mechanism 41 is a mechanism for moving the movement press part 46 in the up-down directions.

The cam shaft 29 is a columnar bar member and is inserted through the cam shaft insertion holes 31 of the light emission support part 21.

The cam 28 is attached to a left end or a center of the cam shaft 29 in such a manner as not to be relatively rotatable. Also, the lever 27 is attached to a right end portion or both end portions of the cam shaft 29 in such a manner as not to be relatively rotatable. When a user rotates the lever 27 clockwise, the cam 28 that rotates together elevates the lower surface of the abutment part 37, which causes the support shafts 32 and the movement press part 46 to be elevated as well, bringing the blood measurement device 10 into an insertion mode to be described below. Meanwhile, when a user rotates the lever 27 counterclockwise, the cam 28 that rotates together no longer presses the lower surface of the abutment part 37, and the biasing force of the springs 34 causes the support shafts 32 and the movement press part 46 to lower, bringing the blood measurement device 10 into a measurement mode to be described below.

Figure 3:
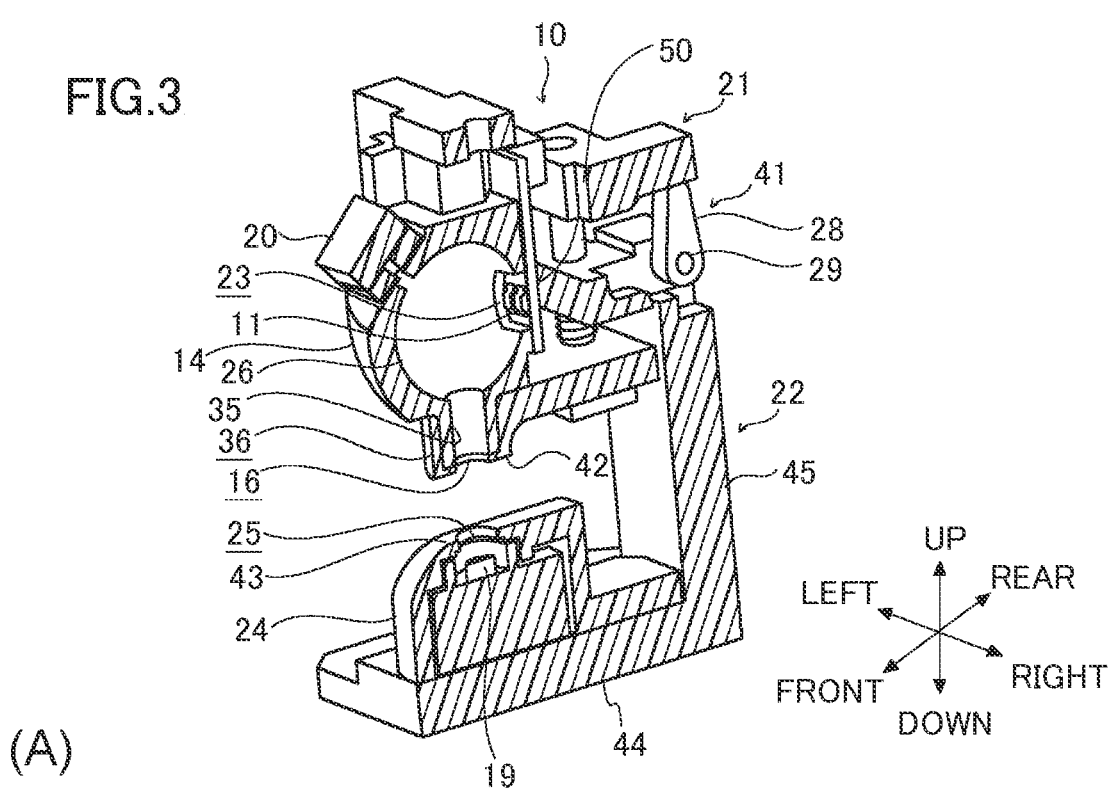
FIG. 3 is a diagram showing the blood measurement device according to the embodiment of the present invention, FIG. 3(A) being a cut-open perspective view and FIG. 3(B) being a side sectional view.
Figure 3:
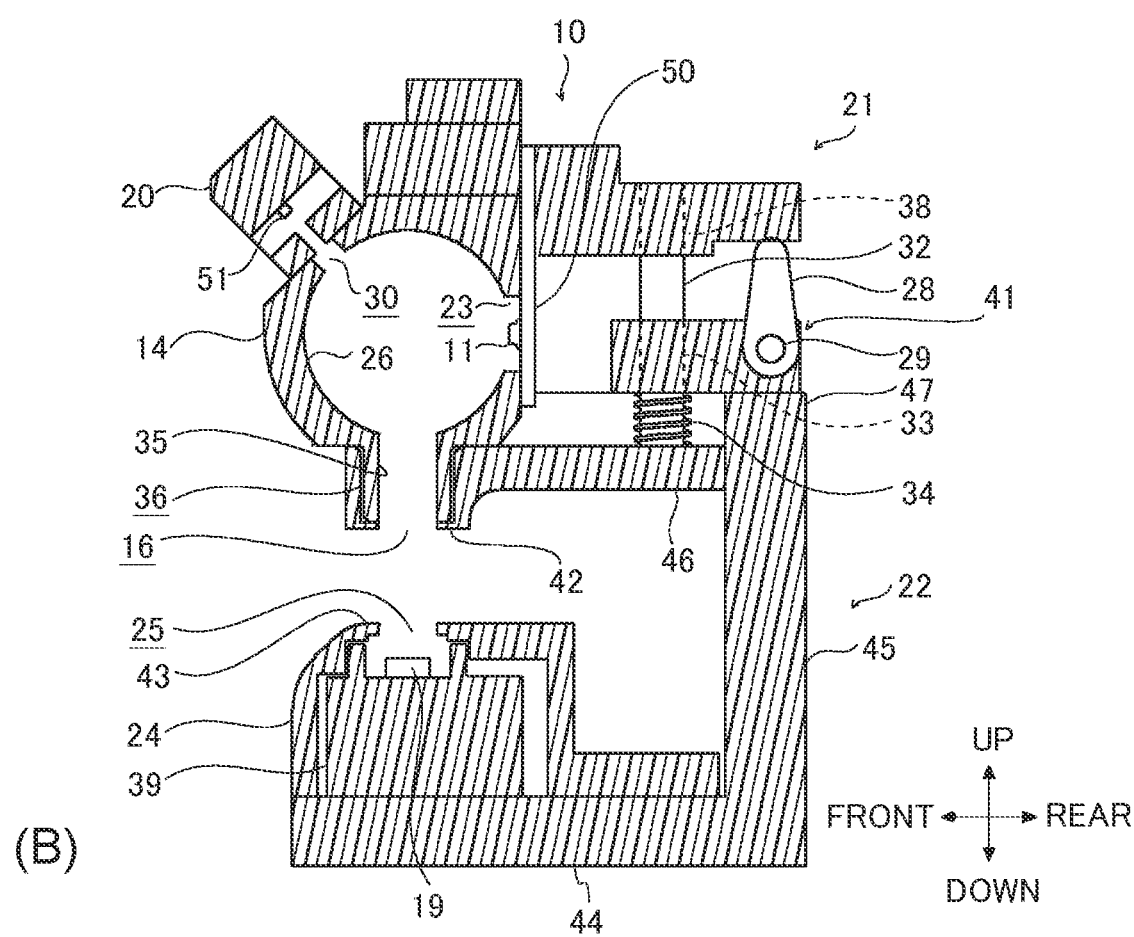

FIG. 3 is a diagram showing the internal configuration of the blood measurement device 10, FIG. 3(A) being a cut-open perspective view and FIG. 3(B) being a side sectional view.

Referring to FIGS. 3(A) and 3(B), a reflection surface 26 is formed inside the integrating sphere part 14. The reflection surface 26 is the inner surface of the integrating sphere part 14 and is in the shape of a spherical or substantially spherical curved surface. The reflection surface 26 is preferably a coarse surface. When the reflection surface 26 is a coarse surface, a light beam can be diffusely reflected by the reflection surface 26, and a light beam diffusely reflected by the reflection surface 26 a plurality of times can be emitted downward uniformly.

The integrating sphere part 14 has a plurality of openings for entry and emission of a light beam. Specifically, a light entry part 23, a light monitor opening part 30, and a light exit part 16 are formed at the integrating sphere part 14.

The light entry part 23 is closed from the outside by a substrate 50, and the light emitting part 11 is situated on the main surface of the substrate 50 which faces the inside of the integrating sphere part 14. As will be described later, a plurality of light emission points that apply light beams of different wavelengths are formed at the light emitting part 11. The light entry part 23 is formed in a right end portion of the reflection surface 26, which is substantially circular in cross section.

The monitor light receiving part 20 is attached to the light monitor opening part 30 from the outside. A monitor light receiving element 51, which is a photodiode, is placed inside the monitor light receiving part 20. The light receiving surface of the monitor light receiving element 51 faces the light monitor opening part 30. The light monitor opening part 30 is formed in an upper left portion of the reflection surface 26.

The light exit part 16 is an opening formed in a lowermost portion of the reflection surface 26. The light exit part 16 is substantially circular when seen from above. Also, as described earlier, the tubular part 35 extends downward from a lower portion of the integrating sphere part 14, and the light exit part 16 is also the opening of the tubular part 35.

A light beam travels as follows inside the integrating sphere part 14. Specifically, a light beam emitted from the light emitting part 11 leftward from a right end portion of the reflection surface 26 is first diffusely reflected at a left end of the reflection surface 26. The light beam diffusely reflected at this location is further diffusely reflected at a different portion of the reflection surface 26. A part of the light beam reaches the monitor light receiving element 51 through the light monitor opening part 30. Meanwhile, another part of the light beam travels downward through the light exit part 16 in a columnar region with a substantially uniform intensity.

As described earlier, the light reception entry part 25 and the light receiving part 19 are situated under the light exit part 16. Thus, the light beam travelling downward through the light exit part 16 is applied to the upper surface of the light receiving part 19 through the light reception entry part 25 in a substantially columnar shape.

Figure 4:
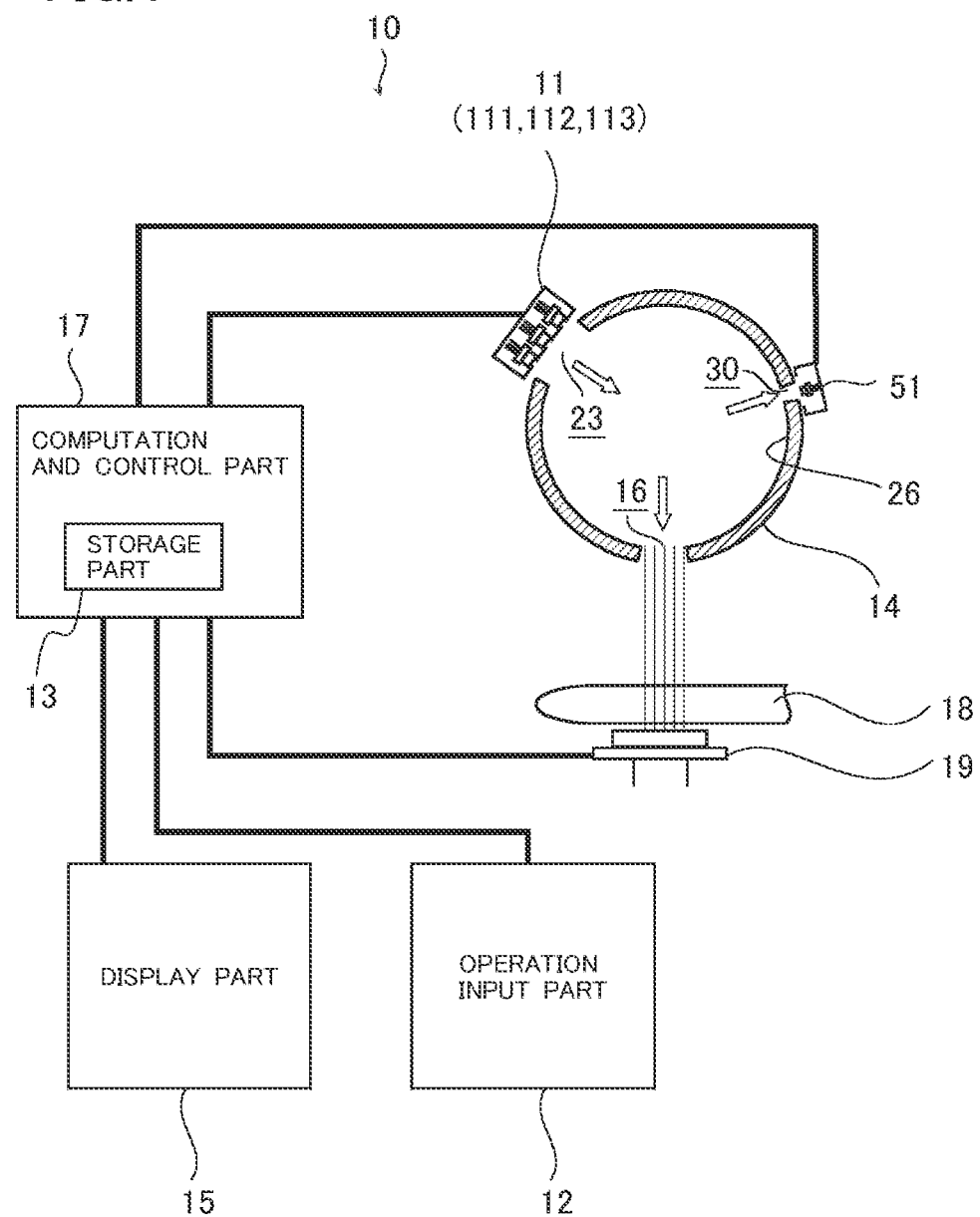
FIG. 4 is a connection diagram showing the blood measurement device according to the embodiment of the present invention.

FIG. 4 is a connection diagram showing the blood measurement device 10.

The blood measurement device 10 has a computation and control part 17, a display part 15, an operation input part 12, the light receiving part 19, the light emitting part 11, and the monitor light receiving element 51, and these constituent members are electrically connected to one another.

The computation and control part 17, which is formed of a CPU, performs various kinds of computation and controls the operation of each part forming the blood measurement device 10. To be more specific, the computation and control part 17 applies a first light beam, a second light beam, and a third light beam from a first light emitting part 111, a second light emitting part 112, and a third light emitting part 113 of the light emitting part 11. In other words, the computation and control part 17 applies two or more light beams from the light emitting part 11. Also, the computation and control part 17 estimates a glucose level using a conversion formula and the like based on electric signals inputted from the light receiving part 19 and the like.

A storage part 13 is, e.g., a semiconductor storage device made of a RAM or a ROM, and stores calculation formulae for calculating a glucose level from an output value from the light receiving part 19, parameters, estimation results, programs for executing a glucose level calculation method, and the like.

The display part 15 is, e.g., a liquid crystal monitor, and the computation and control part 17 may display a calculated glucose level on the display part 15. When the glucose level is displayed on the display part 15, a user using the blood measurement device 10 can know a change in their glucose level in real time.

The operation input part 12 is a part with which a user gives instructions to the computation and control part 17 and is formed of a switch, a touch panel, or the like.

The light receiving part 19 is a semiconductor device made of, for example, a photodiode and has a light receiving part formed to receive the first light beam, the second light beam, and the third light beam transmitting through the measurement site 18 and detect the intensity of the light received. The light receiving part 19 sends the computation and control part 17 signals according to the light reception intensities of the first light beam, the second light beam, and the third light beam.

The light emitting part 11 emits light beams of predetermined wavelengths in order to measure a glucose level. The light emitting part 11 has the first light emitting part 111, the second light emitting part 112, and the third light emitting part 113 that emit light beams of different wavelengths. The first light emitting part 111, the second light emitting part 112, and the third light emitting part 113 are each made of a light emission diode. For example, the wavelength of a first light beam emitted from the first light emitting part 111 is 1310 nm, the wavelength of a second light beam emitted from the second light emitting part 112 is 1450 nm, and the wavelength of a third light beam emitted from the third light emitting part 113 is 1550 nm. The first light beam is a light beam not absorbed by a component in living organisms, while the second and third light beams are light beams absorbed by glucose, protein, and water in living organisms.

The monitor light receiving element 51 receives part of light emitted from the light emitting part 11 and reflected by the reflection surface 26, which is a coarse surface, and sends a signal indicative of the intensity of the received light to the computation and control part 17. The computation and control part 17 controls the output intensity of the light emitting part 11 so that the intensity of the light beam received by the monitor light receiving element 51 may be a predetermined value.

At the integrating sphere part 14, the light entry part 23 and the light exit part 16 are formed at positions sandwiching the center of the reflection surface 26 but not facing each other. This allows a light beam from the light emitting part 11 that enters the integrating sphere part 14 through the light entry part 23 to be diffusely reflected by reflection surface 26 a plurality of times and to be lead out to the measurement site 18 side through the light exit part 16 as a uniform columnar light beam. Also, at the reflection surface 26 of the integrating sphere part 14, the light entry part 23 and the light monitor opening part 30 are situated at positions sandwiching the center of the reflection surface 26 but not facing each other. This configuration allows a light beam diffusely reflected by the reflection surface 26 into the light entry part 23 to be monitored by the monitor light receiving element 51, so that the intensity of the light beam applied through the light entry part 23 can be accurately detected by the monitor light receiving element 51. Further, here, the light exit part 16 and the light monitor opening part 30 are also situated at positions sandwiching the center of the reflection surface 26 but not facing each other.

In the configuration described above, light beams applied from the first light emitting part 111, the second light emitting part 112, and the third light emitting part 113 of the light emitting part 11 become uniform columnar light beams after being reflected by the reflection surface 26 of the integrating sphere part 14 a plurality of times and are emitted to the outside of the integrating sphere part 14 through the light exit part 16. In the present embodiment, three light beams of different wavelengths are emitted from the light emitting part 11 into the integrating sphere part 14, but the light beams are diffusely reflected by the reflection surface 26 of the integrating sphere part 14 and thereby emitted downward in a columnar shape through the light exit part 16.

After that, the light beams transmit through the measurement site 18 and are applied to the light receiving part 19. The light receiving part 19 electrically sends electric signals indicative of the intensities of the light beams to the computation and control part 17. The computation and control part 17 calculates a glucose level based on, e.g., the signals sent from the light receiving part 19.

In the present embodiment, the first light beam, the second light beam, and the third light beam are applied from the light emitting part 11 to the light receiving part 19 along the same optical axis. In other words, the first light beam, the second light beam, and the third light beam have the same propagation path and propagation length inside the measurement site 18.

Because the light beams share the optical axis as described above, a glucose level can be measured accurately. Specifically, according to the Lambert-Beer law, a glucose level is calculated using the following Formula 1:

$$C = -\log 10(I/I0)/(0.434 \times \mu a \times r).$$   Formula 1:

In Formula 1 above, C is a glucose level, I is the power of emitted light, I0 is the power of incident light, μa is the light absorption coefficient of the measurement site 18, and r is an optical path length.

In the present embodiment, the first light beam, the second light beam, and the third light beam have the same optical path length r by sharing the optical axis, and thus, there are fewer unknown numbers to be calculated, which makes it possible to find the glucose level C accurately and easily.

For example, a statistical method can be used as the glucose level calculation method. As an example, a multi-regression curve is created by statistical analysis using glucose levels in blood drawn from users, the reception intensities of light beams, body temperatures, and the like. Then, using the regression curve, an estimated glucose level is calculated from the reception intensities of the light beams and the body temperature.

Figure 5:
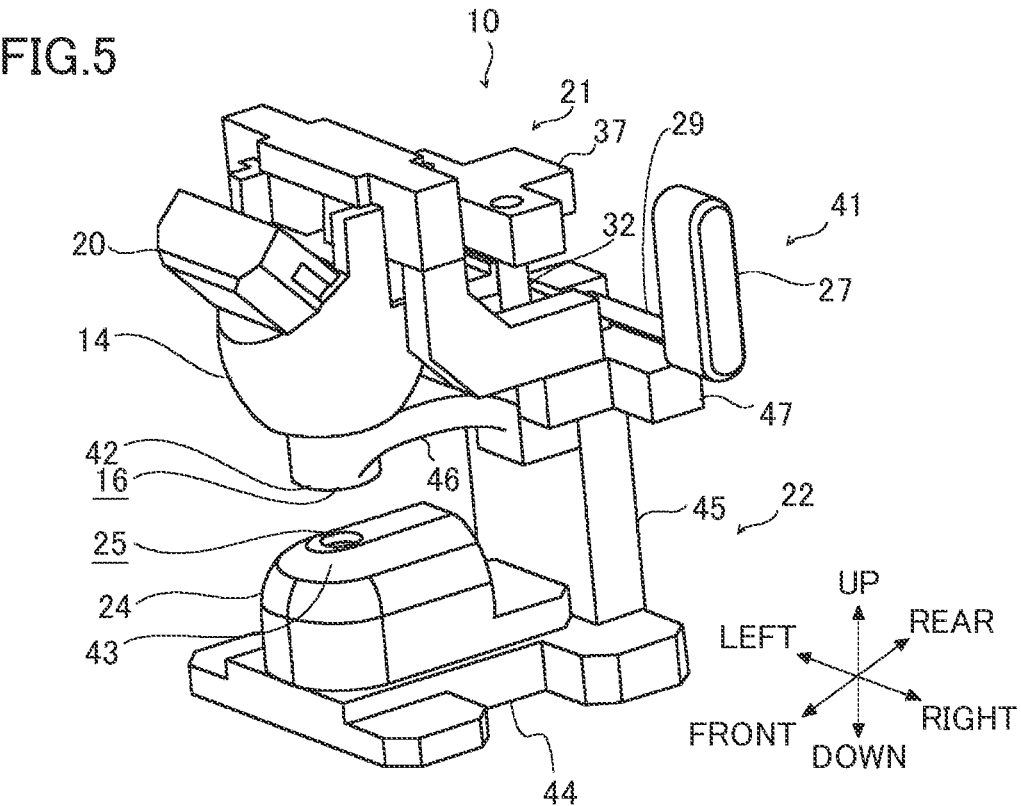
FIG. 5 shows an insertion mode of the blood measurement device according to the embodiment of the present invention, FIG. 5(A) being a perspective view of the blood measurement device seen from the front and FIG. 5(B) being a perspective view of the blood measurement device seen from the rear.
Figure 5:
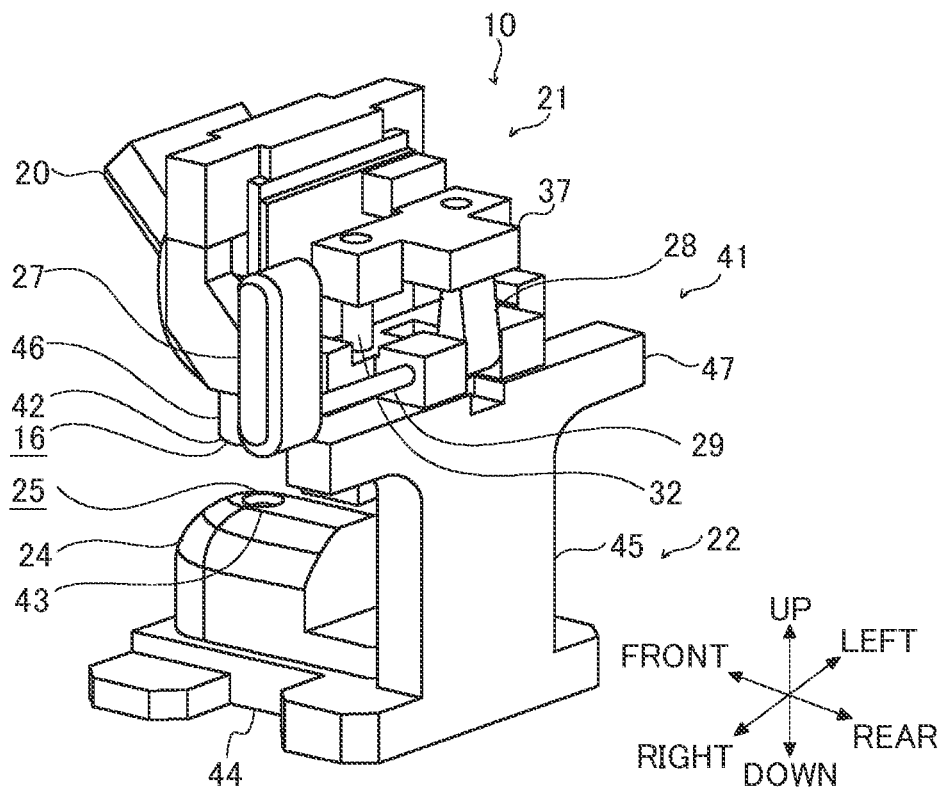
Figure 6:
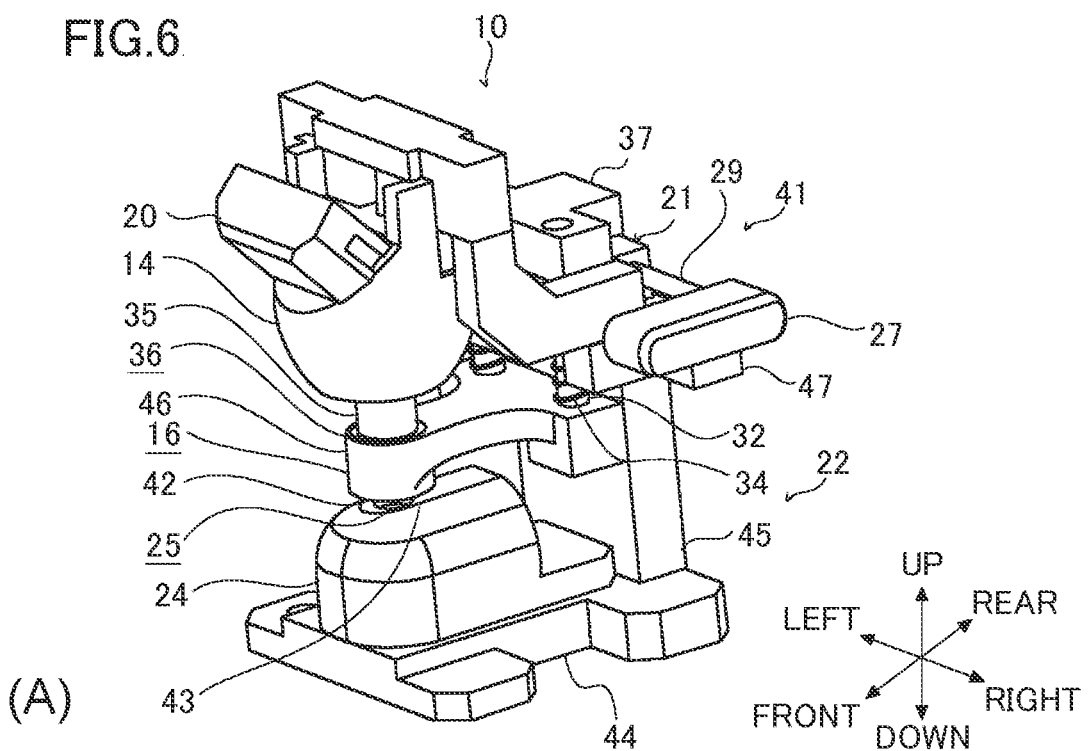
FIG. 6 shows a measurement mode of the blood measurement device according to the embodiment of the present invention, FIG. 6(A) being a perspective view of the blood measurement device seen from the front and FIG. 6(B) being a perspective view of the blood measurement device seen from the rear.
Figure 6:
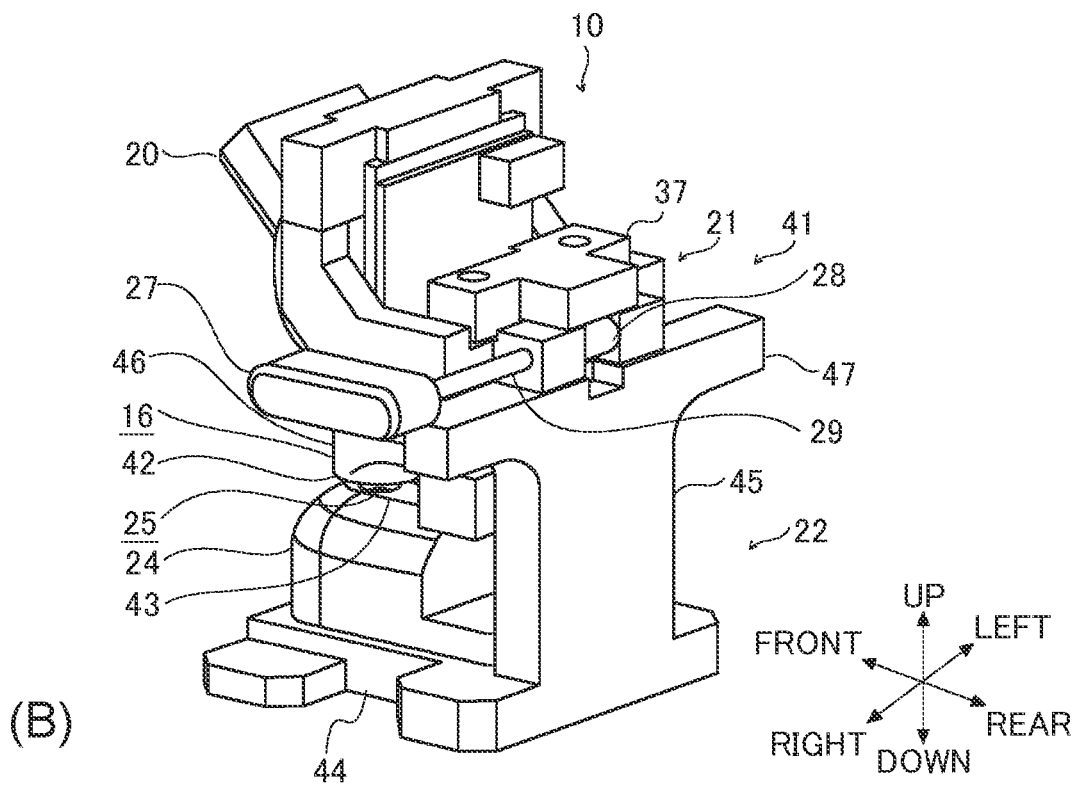

With reference to FIGS. 5 and 6, a description is given of a method for measuring a glucose level of the measurement site 18 using the blood measurement device 10 configured as described above. FIG. 5 shows the insertion mode where a user inserts a finger web as the measurement site 18 into a predetermination location in the blood measurement device 10, and FIG. 6 shows the measurement mode where a glucose level is measured with the finger web.

FIG. 5 shows the insertion mode of the blood measurement device 10, FIG. 5(A) being a perspective view of the blood measurement device 10 seen from the front and FIG. 5(B) being a perspective view of the blood measurement device 10 seen from the rear.

Referring to FIGS. 5(A) and 5(B), in the insertion mode, because the lever 27 is up, the lower surface of the abutment part 37 is lifted upward of the cam 28. Accordingly, the movement press part 46, which is connected to the abutment part 37 via the support shafts 32, is also situated upward. Thus, the movement abutment part 42, which is the lower surface of the movement press part 46, and the light-reception-side abutment part 43, which is the upper surface of the light reception cover part 24, are away from each other greatly. Specifically, the distance by which the movement abutment part 42 and the light-reception-side abutment part 43 are away from each other is equal to or more than the thickness of a finger web as the measurement site 18. Thus, in this mode, a user can easily insert their finger web to between the movement abutment part 42 and the light-reception-side abutment part 43. When the user rotates the lever 27 counterclockwise approximately 90 degrees with their unmeasured hand in this mode, the blood measurement device 10 is brought to the measurement mode shown in FIG. 6.

FIG. 6 shows the measurement mode of the blood measurement device 10, FIG. 6(A) being a perspective view of the blood measurement device 10 seen from the front and FIG. 6(B) being a perspective view of the blood measurement device 10 seen from the rear.

Referring to FIGS. 6(A) and 6(B), when a user rotates the lever 27 counterclockwise toward them, the cam 28 too rotates counterclockwise, and consequently the supporting force exerted by the cam 28 to the abutment part 37 is no longer exerted. As described above, the movement press part 46 is biased downward by the springs 34. Thus, the movement press part 46 lowers until the lower surface of the abutment part 37 abuts against the upper surface of the light emission support part 21. Consequently, the finger web as the measurement site 18, which is not shown here, is pressed into a predetermined thickness between the movement abutment part 42 of the movement press part 46 and the light-reception-side abutment part 43 of the light reception cover part 24.

In this state, the interval between the movement abutment part 42 and the light-reception-side abutment part 43 is no more than a typical thickness of a finger web as the measurement site 18, and is, for example, between 1.5 mm and 3.0 mm, both inclusive. This allows the finger web sandwiched between the movement abutment part 42 and the light-reception-side abutment part 43 to have a predetermined thickness. Thus, even though the thickness of a finger web varies between individuals, the thickness of the finger web can be equalized for the measurement, which allows a glucose level to be measured accurately.

When a light beam is emitted from the light emitting part 11 shown in FIG. 4 in this mode, the emitted light beam is reflected by the reflection surface 26 of the integrating sphere part 14, is then applied to the measurement site 18 through the light exit part 16, transmits through the measurement site 18, and reaches the light receiving part 19. The computation and control part 17 calculates a glucose level based on outputs from the light receiving part 19.

In this state, as shown in FIG. 6(A), even when the movement press part 46 moves downward, a lower end portion of the tubular part 35 is inserted in the insertion hole 36 of the movement press part 46. This can prevent an optical path formed inside the tubular part 35 from being affected by external perturbations.

After the glucose level calculation is completed, the user turns the lever 27 90 degrees clockwise. This brings the blood measurement device 10 into the insertion mode shown in FIG. 5, which means that the movement abutment part 42 and the light-reception-side abutment part 43 are away from each other, allowing the user to remove their finger web from the blood measurement device 10.

Figure 7:
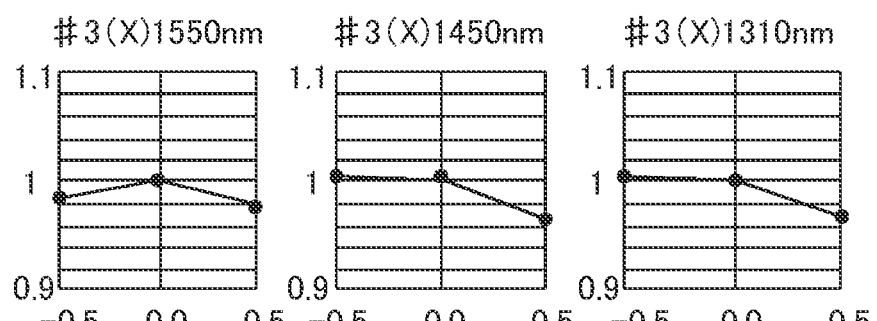
FIG. 7 is graphs showing effects related to the lateral direction by the blood measurement device according to the embodiment of the present invention, FIGS. 7(A), 7(B), and 7(C) showing results for a blood measurement device of a comparative example having no integrating sphere part and FIGS. 7(D), 7(E), and 7(F) showing results for the present embodiment having an integrating sphere part.
Figure 7:
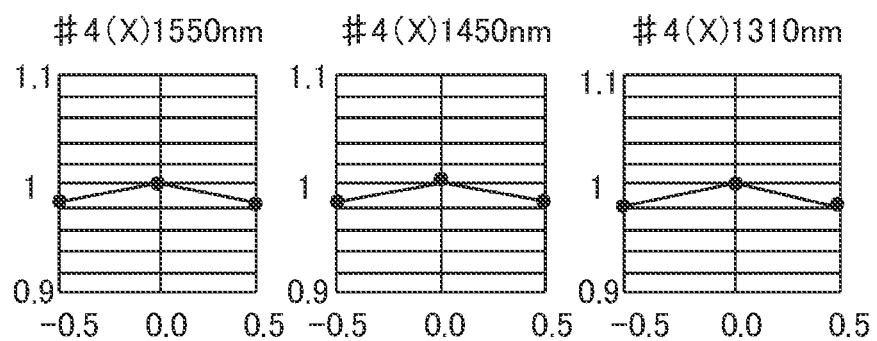

With reference to FIGS. 7 and 8, specific effects offered by the blood measurement device 10 having the integrating sphere part 14 are described.

FIG. 7 is graphs showing effects related to the lateral direction by the blood measurement device 10, i.e., a case where a light beam shifts in the lateral direction. In each graph in FIG. 7, the horizontal axis represents the distance of a positional change of the optical axis in the lateral direction, and the vertical axis represents the rate of change in the intensity of the light beam. FIGS. 7(A), 7(B), and 7(C) show results for a blood measurement device of a comparative example having no integrating sphere part. Meanwhile, FIGS. 7(D), 7(E), and 7(F) show results for the blood measurement device 10 of the present embodiment having the integrating sphere part. Also, FIGS. 7(A) and 7(D) show results for a light beam of a wavelength of 1550 nm, FIGS. 7B and 7E show results for a light beam of a wavelength of 1450 nm, and FIGS. 7(C) and 7(F) show results for a light beam of a wavelength of 1310 nm.

Referring to FIGS. 7(A), 7(B), and 7(C), in the comparative example in which the integrating sphere part 14 is not interposed in the optical path, the light amount greatly changes due to the displacement of the optical axis. In particular for the wavelengths 1450 nm and 1310 nm, referring to FIGS. 7(B) and 7(C), the decrease in light amount due to the displacement of the optical axis is approximately 0.03 and is large.

Meanwhile, referring to FIGS. 7(D), 7(E), and 7(F), in the blood measurement device 10 of the present embodiment having the integrating sphere part 14 in the optical path, even if the optical axis is displaced, there is no large change in the amount of light. Referring to FIGS. 7(D), 7(E), and 7(F) in particular, the amount of decrease in the light amount due to the displacement of the optical axis is approximately 0.01 to 0.02 and is small.

FIG. 8 is graphs showing effects related to the longitudinal direction by the blood measurement device 10, i.e., a case of a shift from the optical axis in the longitudinal direction. In each graph in FIG. 8, the horizontal axis represents the distance of a positional change of the optical axis in the longitudinal direction, and the vertical axis represents the rate of change in the intensity of a light beam. FIGS. 8(A), 8(B), and 8(C) show results for the blood measurement device of the comparative example having no integrating sphere part. Meanwhile, FIGS. 8(D), 8(E), and 8(F) show results for the blood measurement device 10 of the present embodiment having the integrating sphere part. Also, FIGS. 8(A) and 8(D) show results for a light beam of a wavelength of 1550 nm, FIGS. 8(B) and 8(E) show results for a light beam of a wavelength of 1450 nm, and FIGS. 8(C) and 8(F) show results for a light beam of a wavelength of 1310 nm.

Referring to FIGS. 8(A), 8(B), and 8(C), in the comparative example in which the integrating sphere part 14 is not interposed in the optical path, the light amount greatly changes due to the displacement of the optical axis. Referring to FIG. 8(B) in particular, the amount of light greatly changes in such a manner as to be positively correlated to the longitudinal displacement of the optical axis. Also, referring to FIG. 8(C), the amount of light greatly changes in such a manner as to be negatively correlated to the longitudinal displacement of the optical axis.

Meanwhile, referring to FIGS. 8(D), 8€, and 8(F), in the blood measurement device 10 of the present embodiment having the integrating sphere part 14 in the optical path, even if the optical axis is displaced, there is no large change in the amount of light. Referring to FIGS. 8(D), 8(E), and 8(F) in particular, the amount of decrease in the light amount due to the displacement of the optical axis is approximately 0.02 and is small.

Judging from the above, referring to FIG. 4, in the blood measurement device 10 having the integrating sphere part 14 and causing a light beam diffusely reflected by the reflection surface 26 of the integrating sphere part 14 to be applied uniformly in a columnar shape through the light exit part 16, even if the optical axis is displaced, the amount of light received by the light receiving part 19 can be prevented from changing due to the displacement of the optical axis. Thus, a glucose level can be measured accurately.

Each embodiment described above can primarily provide the following effects.

Referring to FIG. 4, because the integrating sphere part 14 is interposed in the optical path, a light beam uniformed by being reflected by the reflection surface 26 of the integrating sphere part 14 can be uniformly applied to the measurement site 18 in a columnar region. This helps prevent a light beam applied to the light receiving element from being drastically decreased in intensity even if the position of the light emitting element that applies the light beam is somewhat displaced from its designed location.

Referring to FIG. 4, if a first light beam and a second light beam having different wavelengths are applied from the first light emitting part 111 and the second light emitting part 112, an actuator is usually needed to move the first light emitting part 111 and the second light emitting part 112 onto the optical axis. However, in the present embodiment, as described above, a light beam uniformed by being reflected by the reflection surface 26 of the integrating sphere part 14 is uniformly applied to the measurement site 18 in a columnar region, and thus, a plurality of light beams of different wavelengths can be applied toward the measurement site 18 and the light receiving part 19 along the optical path without needing an actuator.

Referring to FIG. 4, because the reflection surface 26 of the integrating sphere part 14 has a spherical surface shape, a light beam reflected by the reflection surface 26 a plurality of times can be uniformly applied toward the measurement site 18 and the light receiving part 19 through the light exit part 16.

Referring to FIG. 4, the intensity of a light beam reflected by the reflection surface 26 is measured with the monitor light receiving part 20, and based on the result, the computation and control part 17 adjusts the intensity of light applied from the light emitting part 11, thereby allowing light applied to the measurement site 18 and the light receiving part 19 to have a predetermined intensity.

Referring to FIG. 4, when the reflection surface 26 of the integrating sphere part 14 is a coarse surface, a light beam is diffusely reflected by the reflection surface 26 effectively, and a columnar light beam can be applied toward the measurement site 18 and the light receiving part 19 through the light exit part 16.

Referring to FIGS. 5 and 6, the blood measurement device 10 has the movement press part 46 that moves between the insertion mode and the measurement mode, and the movement press part 46 can make the measurement site 18 have a predetermined thickness by pressing the measurement site 18 in the measurement mode, which allows blood-related parameters such as a blood sugar level to be accurately measured.

Referring to FIG. 5, a user can freely change the relative distance between the light emission support part 21 and the light reception support part 22 by operating the lever 27 and thereby rotating the cam 28.

Referring to FIG. 2, because the movement press part 46 is lowered by the biasing force exerted by the springs 34, turning of the cam 28 allows the distance between the movement abutment part 42 and the light-reception-side abutment part 43 to have a predetermined length.

Referring to FIGS. 5 and 6, in the insertion mode and the measurement device, the tubular part 35 is inserted in the insertion hole 36, so that the optical path can be covered by the tubular part 35.

Referring to FIGS. 5 and 6, the measurement site 18 can be easily inserted between the movement abutment part 42 and the light-reception-side abutment part 43 in the insertion mode, and the measurement site 18 is sandwiched between the movement abutment part 42 and the light-reception-side abutment part 43 to have a certain thickness of the measurement site 18 in the measurement mode, so that a glucose level can be accurately measured.

Although the embodiment of the present invention is thus described, the present invention is not limited to the above and can be modified without departing from the gist of the present invention. Also, the modes described above can be combined with each other.

Referring to FIG. 3(A), the reflection surface 26 of the integrating sphere part 14 does not necessarily have to be perfectly spherical and may be a curved shape that resembles a sphere shape.

Although a blood glucose level is calculated with the blood measurement device 10 in the present embodiment, a physical quantity other than a glucose level can be measured with the blood measurement device 10.

REFERENCE SINGS LIST 10 blood measurement device
11 light emitting part
111 first light emitting part
112 second light emitting part
113 third light emitting part
12 operation input part
13 storage part
14 integrating sphere part
15 display part
16 light exit part
17 computation and control part
18 measurement site
19 light receiving part
20 monitor light receiving part
21 light emission support part
22 light reception support part
23 light entry part
24 light reception cover part
25 light reception entry part
26 reflection surface
27 lever
28 cam
29 cam shaft
30 light monitor opening part
31 cam shaft insertion hole
32 support shaft
33 support shaft insertion hole
34 spring
35 tubular part
36 insertion hole
37 abutment part
38 abutment insertion hole
39 light reception placement part
41 moving mechanism
42 movement abutment part
43 light-reception-side abutment part
44 seat part
45 pillar part
46 movement press part
47 light reception support upper part
48 notch part
49 guide part
50 substrate
51 monitor light receiving element

The invention claimed is:

1. A blood measurement device that measures a component contained in blood based on a light beam that has transmitted through or been reflected by a measurement site, the blood measurement device comprising:
    a light emitting part that emits the light beam that is to transmit through or be reflected by the measurement site;
    a light receiving part that receives the light beam that has transmitted through or been reflected by the measurement site;
    an integrating sphere part interposed in an optical path along which the light beam emitted from the light emitting part reaches the light receiving part, the integrating sphere part having formed inside a reflection surface that reflects the light beam;
    a light entry part which is an opening provided at the integrating sphere part and through which the light beam applied from the light emitting part enters an inside of the integrating sphere part;
    a light exit part which is an opening provided at the integrating sphere part and through which the light beam reflected by the reflection surface of the integrating sphere part is emitted from the integrating sphere part toward the measurement site;
    a light monitor opening part which is an opening provided at the integrating sphere part and through which part of the light beam entering the integrating sphere part through the light entry part and getting reflected by the reflection surface is emitted to an outside;
    a monitor light receiving part that receives the light beam emitted through the light monitor opening part; and
    a computation and control part that controls intensity of the light beam emitted from the light emitting part based on an output from the monitor light receiving part.

2. The blood measurement device according to claim 1, wherein
    the light emitting part applies a first light beam and a second light beam from a first light emitting part and a second light emitting part, respectively, the second light beam having a wavelength different from that of the first light beam,
    the reflection surface of the integrating sphere part reflects the first light beam and the second light beam,
    through the light exit part of the integrating sphere part, the first light beam and the second light beam are applied toward the measurement site and the light receiving part, and
    the light receiving part receives the first light beam and the second light beam.

3. The blood measurement device according to claim 1, wherein
    the reflection surface of the integrating sphere part has a spherical surface shape.

4. The blood measurement device according to claim 1, wherein
    the reflection surface is a coarse surface.

5. The blood measurement device according to claim 1, wherein
    the light emitting part applies a first light beam, a second light beam, and a third light beam from a first light emitting part, a second light emitting part, and a third light emitting part, respectively, the second light beam having a wavelength different from that of the first light beam, the third light beam having a wavelength different from those of the first and second light beams,
    the reflection surface of the integrating sphere part reflects the first light beam, the second light beam, and the third light beam,
    through the light exit part of the integrating sphere part, the first light beam, the second light beam, and the third light beam are applied toward the measurement site and the light receiving part,
and
    the light receiving part receives the first light beam, the second light beam, and the third light beam.

* * * * *